(12) United States Patent
Khatri et al.

(10) Patent No.: US 7,544,665 B2
(45) Date of Patent: Jun. 9, 2009

(54) SYNTHESIS USING PEPTIDE INTERMEDIATE FRAGMENTS

(75) Inventors: Hiralal N. Khatri, Louisville, CO (US); Yeun-Kwei Han, Louisville, CO (US); David A. Johnston, Louisville, CO (US); L. Mark Hodges, Longmont, CO (US)

(73) Assignee: Roche Colorado Corporation, Boulder, CO (US)

( * ) Notice: Subject to any disclaimer, the term of this patent is extended or adjusted under 35 U.S.C. 154(b) by 315 days.

(21) Appl. No.: 11/322,394

(22) Filed: Dec. 30, 2005

(65) Prior Publication Data

US 2006/0173163 A1   Aug. 3, 2006

Related U.S. Application Data

(60) Provisional application No. 60/640,716, filed on Dec. 30, 2004.

(51) Int. Cl.
*A61K 38/00* (2006.01)
*C07K 1/02* (2006.01)

(52) U.S. Cl. .................... 514/13; 530/324; 530/330

(58) Field of Classification Search .............. None
See application file for complete search history.

(56) References Cited

U.S. PATENT DOCUMENTS

| 5,464,933 | A | 11/1995 | Bolognesi et al. |
|---|---|---|---|
| 5,656,480 | A | 8/1997 | Wild et al. |
| 6,015,881 | A | 1/2000 | Kang et al. |
| 6,281,331 | B1 | 8/2001 | Kang et al. |
| 6,281,335 | B1 | 8/2001 | do Couto et al. |
| 6,469,136 | B1 * | 10/2002 | Bray et al. ............ 530/300 |
| 6,479,055 | B1 | 11/2002 | Bolognesi et al. |
| 2004/0209999 | A1 | 10/2004 | Bohling et al. |
| 2006/0276624 | A1 | 12/2006 | Khatri et al. |

FOREIGN PATENT DOCUMENTS

EP   1 452 538 A   9/2004

OTHER PUBLICATIONS

Albericio, F., (Jun. 2004) "Developments in Peptide and Amide Synthesis," Current Opinion in Chemical Biology, vol. 8, No. 3, pp. 211-221.
Bruckdorfer, T., et al., (Feb. 2004) "From Production of Peptides in Milligram Amounts for Research to Multi-tons Quantities for Drugs of the Future," Current Pharmaceutical Biotechnology, vol. 5, No. 1, pp. 29-43.
Riniker, et al., (1993) Tetrahedron Letters 49:9307-9320.
Lloyd-Williams, et al., (1993) Tetrahedron Letters 49:11065-11133.
Andersson, et al., (2000) Biopolymers 55:227-250.
Bray, B.L., (2003) Nature Rev., 2:587-593.
International Search Report for International Application No. PCT/EP2005/013852, mailed Jun. 19, 2006.

\* cited by examiner

*Primary Examiner*—Christopher R. Tate
*Assistant Examiner*—Roy Teller
(74) *Attorney, Agent, or Firm*—Brian L. Buckwalter

(57) ABSTRACT

Methods for the solid phase synthesis of T-1249 peptides and peptide intermediates, in particular methods involving synthesizing T-1249 peptide intermediates at low loading factors to produce products having excellent purity and yield.

6 Claims, No Drawings

SEQUENCE LISTING

<160> NUMBER OF SEQ ID NOS: 4

<210> SEQ ID NO 1
<211> LENGTH: 39
<212> TYPE: PRT
<213> ORGANISM: Artificial
<220> FEATURE:
<223> OTHER INFORMATION: Chemically synthesized peptide fragment

<400> SEQUENCE: 1

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 2
<211> LENGTH: 20
<212> TYPE: PRT
<213> ORGANISM: Artificial
<220> FEATURE:
<223> OTHER INFORMATION: Chemically synthesized peptide fragment

<400> SEQUENCE: 2

Trp Gln Glu Trp Glu Gln Lys Ile Thr Ala Leu Leu Glu Gln Ala Gln
1               5                   10                  15

Ile Gln Gln Glu
            20

<210> SEQ ID NO 3
<211> LENGTH: 18
<212> TYPE: PRT
<213> ORGANISM: Artificial
<220> FEATURE:
<223> OTHER INFORMATION: Chemically synthesized peptide fragment

<400> SEQUENCE: 3

Lys Asn Glu Tyr Glu Leu Gln Lys Leu Asp Lys Trp Ala Ser Leu Trp
1               5                   10                  15

Glu Trp

```
<210> SEQ ID NO 4
<211> LENGTH: 19
<212> TYPE: PRT
<213> ORGANISM: Artificial
<220> FEATURE:
<223> OTHER INFORMATION: Chemically synthesized peptide fragment

<400> SEQUENCE: 4

Lys Asn Glu Tyr Glu Leu Gln Lys Leu Asp Lys Trp Ala Ser Leu Trp
1               5                   10                  15

Glu Trp Phe
```

SYNTHESIS USING PEPTIDE INTERMEDIATE FRAGMENTS

REFERENCE TO RELATED APPLICATION

This application is a non-provisional application with claims priority to U.S. Provisional Application No. 60/640,716, entitled IMPROVED SYNTHESIS USING PEPTIDE INTERMEDIATE FRAGMENTS, filed on Dec. 30, 2004, which is herein incorporated by reference in its entirety.

FIELD OF THE INVENTION

The invention relates to methods for preparing T-1249 peptides using solid- and solution-phase processes, in addition to T-1249 intermediate peptide fragments that can be used in these methods. More particularly, the invention relates to the preparation of T-1249 peptides using two fragments that are synthesized using a solid phase approach.

BACKGROUND OF THE INVENTION

Many methods for peptide synthesis are described in the literature (for examples, see U.S. Pat. No. 6,015,881; Mergler et al. (1988) Tetrahedron Letters 29:4005-4008; Mergler et al. (1988) Tetrahedron Letters 29:4009-4012; Kamber et al. (eds), Peptides, Chemistry and Biology, ESCOM, Leiden (1992) 525-526; Riniker et al. (1993) Tetrahedron Letters 49:9307-9320; Lloyd-Williams et al. (1993) Tetrahedron Letters 49:11065-11133; and Andersson et al. (2000) Biopolymers 55:227-250. The various methods of synthesis are distinguished by the physical state of the phase in which the synthesis takes place, namely liquid phase or solid phase.

In solid phase peptide synthesis (SPPS), an amino acid or peptide group is bound to a solid support resin. Then, successive amino acids or peptide groups are attached to the support-bound peptide until the peptide material of interest is formed. The support-bound peptide is then typically cleaved from the support and subject to further processing and/or purification. In some cases, solid phase synthesis yields a mature peptide product; in other cases the peptide cleaved from the support (i.e., a "peptide intermediate fragment") is used in the preparation of a larger, mature peptide product.

Peptide intermediate fragments generated from solid phase processes can be coupled together in a liquid phase synthetic process (herein referred to as "solution phase synthesis"). Solution phase synthesis can be particularly useful in cases where the synthesis of a useful mature peptide by solid phase is either impossible or not practical. For example, in solid phase synthesis, longer peptides eventually may adopt an irregular conformation while still attached to the solid support, accordingly resulting in partial or entire loss of activity in the final product. Also, as the peptide chain becomes longer on the support resin, the efficiency of process steps such as coupling and deprotection may be compromised. This, in turn, can result in longer processing times to compensate for these problems, in addition to incremental losses in starting materials, such as activatable amino acids, co-reagents, and solvents. These problems can increase as the length of the peptide increases, and therefore, it is relatively uncommon to find mature peptides of greater than 30 amino acids in length synthesized using only a solid phase procedure.

In solution phase coupling, two peptide intermediate fragments, or a peptide intermediate fragment and a reactive amino acid, are coupled in an appropriate solvent, and usually in the presence of additional reagents that promote the efficiency and quality of the coupling reaction. The peptide intermediate fragments are reactively arranged so the N-terminal of one fragment becomes coupled to the C-terminal of the other fragment, or vice versa. In addition, side chain protecting groups, which are present during solid phase synthesis, are commonly retained on the fragments during solution phase coupling to ensure the specific reactivity of the terminal ends of the fragments. These side chain protecting groups are typically not removed until a mature peptide has been formed.

For the synthesis of very large peptides, it is not uncommon for multiple solution phase coupling steps to be performed using three or four or more peptide intermediate fragments. While the general concept of end-to-end coupling reactions in solution phase reactions is generally theoretically straightforward when multiple peptide intermediate fragments are used, in practice this is rarely the case. Various factors, such as impurities and peptide yield, can have a significant affect on the quality and yield of a full-length peptide. Therefore, peptide synthesis using hybrid schemes are often challenging, and in many cases it is difficult to predict what problems are be inherent in a synthesis scheme until the actual synthesis is performed.

In some cases, solution phase synthesis can be affected by a lack of purity of the peptide intermediate fragments following solid phase synthesis. In this regard, it may be necessary to subject peptide intermediate fragments to a purification step prior to coupling the fragments in a solution phase process. The purification, in turn, can cause a reduction in the yield of the peptide intermediate fragment, and accordingly, the final peptide product.

Also, the yield of the mature peptide is inversely proportional to the number of solution phase steps that are required to synthesize the mature peptide. In some cases, three, four, or more than four solution phase steps utilizing peptide intermediate products may be required to generate a mature peptide. Every additional solution phase coupling step can result in a diminished return of full-length peptide product. Therefore, to improve the overall yield, it is generally desirable to minimize the steps that are involved in coupling.

Modest improvements in one or more steps in the overall synthetic scheme can amount to significant improvements in the preparation of the mature peptide. Such improvements can lend to a large overall saving in time and reagents, and can also significantly improve the purity and yield of the final product.

While the discussion of the importance of improvements in hybrid synthesis is applicable to any sort of peptide produced using these procedures, it is of particular import in the context of peptides that are therapeutically useful and that are manufactured on a scale for commercial medical use. While the synthesis of small molecule pharmaceuticals can be relatively inexpensive, the cost of synthesis of larger biomolecular pharmaceuticals, such as therapeutic peptides, in comparison can be vastly higher. Because of the cost of reagents, synthesis time, in addition to other factors, very small improvements in the synthetic process of these larger biomolecular pharmaceuticals can have a significant impact on whether it is even economically feasible to produce such a pharmaceutical. Such improvements are necessary due to these high production costs for larger biomolecular pharmaceuticals as supported by the fact that, in many cases, there are few, if any, suitable therapeutic alternatives for these types of larger biomolecular pharmaceuticals.

This is clearly seen in the case of therapeutic peptides that are used for the treatment of immunodeficiency diseases caused by retroviral infection. Peptides having anti-retroviral activity can act in different ways, including by preventing fusion of the viral particle with the host immune cell. There is a great need for these novel and effective therapeutic peptides because, in many cases, traditionally used anti-virals become ineffective for the treatment of these diseases because of viral resistance due to mutation.

One promising class of therapeutic peptides useful for combating immunodeficiency diseases is fusion inhibitors. These types of therapeutic peptides can reduce viral titer, and significantly improve the quality of life in patients having immunodeficiency diseases. For example, the FUZEON® peptide (also known as enfuvirtide or T-20), which is a synthetic, 36-amino-acid peptide, the hybrid peptide T-1249, and derivatives and counterparts of these peptides, have proven beneficial as fusion inhibitors in the treatment of the human immunodeficiency virus (HIV) and the acquired immune deficiency syndrome (AIDS). The FUZEON® peptide and its derivatives are the first inhibitors of HIV to demonstrate consistent, potent activity in persons infected with HIV. Kilby et al. (1998) *Nat Med* 4:1302 and Kilby et al. (2002) *AIDS Res Hum Retroviruses* 18:685.

Fusion inhibitors such as the T-20 and T-1249 peptides bind to a region of the glycoprotein 41 envelope of HIV type 1 (HIV-1) that is involved in the fusion of the virus with the membrane of the CD4+ host cell. Wild et al. (1993) *AIDS Res. Hum. Retroviruses* 9:1051. Fusion inhibitors remain outside the cell and block HIV-1 prior to HIV-1 entering the cell. The FUZEON® peptide and its derivatives minimize drug interactions, side effects and cytotoxicity by potently and selectively inhibiting HIV-1 in vitro.

In addition to these concerns, issues relating to product recovery and product purity for the large-scale production of peptides, as well as reagent handling, storage and disposal, can greatly impact the feasibility of the peptide synthesis scheme. Thus, there is a continuing need for peptide synthesis processes capable of efficiently producing peptide materials of commercial interest in large batch quantities with improved yields. Recovery of cleaved peptide from a support resin after solid phase synthesis of the peptide is one aspect of the synthesis in which improvement is needed.

SUMMARY OF THE INVENTION

The present invention relates to the preparation of T-1249 peptides that are synthesized using a solid and solution phase ("hybrid") approach. Generally, the approach includes synthesizing two different T-1249 peptide intermediate fragments (SEQ ID NO:2 and SEQ ID NO:3 or counterparts thereof) using solid phase chemistry. According to some inventive aspects, it has been found that following solid phase synthesis, these specific T-1249 intermediate sequences lend themselves particularly well to solution phase coupling steps. In addition, it has also been found that solid phase steps leading to the formation of these peptide intermediate fragments can be inventively modified to significantly improve the yield and purity of these intermediate fragments. This improved yield and purity is carried over into the solution phase coupling steps, thereby improving the entire synthetic process.

The methods of the invention and peptide intermediate fragments described herein are particularly advantageous, especially because it makes the T-1249 synthesis process more efficient in a number of ways. In particular, the solid phase synthesis steps leading to the formation of T-1249 peptide intermediate products SEQ ID NO:2 or SEQ ID NO:3 utilize a support resin having a first amino acid coupled to the support at a loading factor that is lower than what is traditionally used in standard solid phase techniques. Favorably, it has been found that using this lower loading factor, the SEQ ID NO:2 or SEQ ID NO:3 T-1249 peptide intermediate products, which are atypically long solid phase synthesized fragments, can be produced with improved yield and improved purity.

The improved purity and yield, significantly improves conditions for solution phase coupling steps, thereby resulting in improvement for the overall synthesis of T-1249

Until now, most successful T-1249 synthesis approaches have utilized solution phase coupling wherein three, or more than three peptide intermediate fragments are prepared by solid phase synthesis. These intermediate fragments are then used in solution phase coupling reactions to prepare the final T-1249 mature product. While some advantages of a three (or more) fragment approach may be generally seen with regard to a higher quality of solid phase synthesis of the intermediates, this is not necessarily the case with some T-1249 fragments. In particular, it has been difficult to synthesize the T-1249 peptide intermediate fragments consisting of residues 27-38, and consisting of residues 13-26 with good purity. Also, impurities associated with intermediate fragments are potentially present in three fragment approaches using particular solvents for isolation.

Another downside is that a three (or more) fragment approach involves more isolation and purification steps compared to a two-fragment approach, and these additional steps generally increase processing time and can subsequently reduce the overall yield of the synthesis reaction.

Because the present invention utilizes only two peptide intermediate fragments prepared via solid phase synthesis, one clear advantage is that the processing times are reduced and the elimination of processing steps can result in a more efficient use of materials and reagents. This is particularly important in the synthesis of T-1249, as it is a relatively long peptide that includes five tryptophan (W) residues, which are costly reagents in solid phase synthesis.

However, a potential disadvantage with a two fragment approach is that the synthesis of longer intermediate fragments by solid phase synthesis can be complicated and often lead to serious purity and/or recovery problems. Despite this, as stated, the present invention demonstrates that the method of choosing intermediate peptide fragments having a sequence based on SEQ ID NO:2 or SEQ ID NO:3 and then synthesizing these fragments by solid phase synthesis using a low resin loading factor, successfully allows the intermediate fragments to be produced with good yield and purity. Such an achievement is rather remarkable in view of conventional approaches for synthesizing peptides using combined solid phase and solution phase approaches.

The invention is also advantageous in that other aspects of peptide purity are improved. In particular, intermediate peptide fragments having a sequence according to SEQ ID NO:2 or SEQ ID NO:3 do not include an N-terminal glutamic acid (E) residue. To the extent that either intermediate fragment includes a glutamic acid residue, the residue either is positioned within the sequence or at the C-terminus of the intermediate fragment. It has been found that the purity of intermediate fragments can be significantly higher when using fragments having these general sequential arrangements of amino acids (such as in SEQ ID NO:2 and SEQ ID NO:3), inasmuch as a fragment with glutamic acid at the N-terminus tends to include more pyroglutamic acid impurities.

Therefore, in some aspects, the invention provides a method for preparing a peptide intermediate fragment for the synthesis of a T-1249 peptide that includes the steps of (a) providing a solid phase synthesis support resin having a first amino acid coupled to the residue that is glutamic acid (E), wherein the glutamic acid is coupled at a loading factor of 0.5 or less; preferably the glutamic acid is coupled at a loading factor between 0.2 and 0.5; (b) coupling subsequent amino acids to the first amino acid on the coupled support to provide the following sequence: Ac-WQEWEQKITALLEQA-QIQQE-[Support]; (c) removing the Ac-WQEWEQKI-TALLEQAQIQQE (SEQ ID NO:2) peptide intermediate from the support in a cleavage reaction; and then using the Ac-WQEWEQKITALLEQAQIQQE (SEQ ID NO:2) peptide intermediate for the synthesis of a peptide that has all or a portion of Ac-WQEWEQKITALLEQA-QIQQEKNEYELQKLDKWASLWEWF (SEQ ID NO:1).

In other aspects, the invention provides a preparing a peptide intermediate fragment for the synthesis of a T-1249 peptide that includes the steps of (a) providing a solid phase synthesis support resin having a first amino acid coupled to the residue that is tryptophan (W), wherein the tryptophan is coupled at a loading factor of 0.5 or less; preferably the tryptophan is coupled at a loading factor between 0.2 and 0.5; (b) coupling subsequent amino acids to the first amino acid on the coupled support to provide the following sequence: KNEYELQKLDKWASLWEW-[Support]; (c) removing the KNEYELQKLDKWASLWEW (SEQ ID NO:3) peptide intermediate from the support in a cleavage reaction; and then using the KNEYELQKLDKWASLWEW (SEQ ID NO:3) peptide intermediate for the synthesis of a peptide that has all or a portion of Ac-WQEWEQKITALLEQA-QIQQEKNEYELQKLDKWASLWEWF (SEQ ID NO:1).

Most preferably, invention provides a method for preparing a T-1249 peptide that includes the steps of (a) providing peptide intermediate fragments having the sequences Ac-WQEWEQKITALLEQAQIQQE (SEQ ID NO:2) and KNEYELQKLDKWASLWEW (SEQ ID NO:3), wherein the peptide intermediate fragments have been synthesized on solid supports utilizing a loading factor 0.5 or less; preferably using a loading factor between 0.2 to 0.5; (b) in solution phase, reacting the KNEYELQKLDKWASLWEW (SEQ ID NO:3) peptide with a phenylalaninamide residue to provide the sequence KNEYELQKLDKWASLWEWF (SEQ ID NO:4); and (c) in solution phase, reacting the Ac-WQEWEQKI-TALLEQAQIQQE (SEQ ID NO:2) peptide with the KNEYELQKLDKWASLWEWF (SEQ ID NO:4) peptide to provide the Ac-WQEWEQKITALLEQA-QIQQEKNEYELQKLDKWASLWEWF (SEQ ID NO:1) peptide.

In other aspects, in the coupling step the first amino acid is present on the support at a loading factor of less than 0.5. In other aspects, in the coupling step the first amino acid is present on the support at a loading factor in the range of 0.2-0.45, or a loading factor in the range of 0.25-0.40.

In yet other aspects, solid phase synthesis is carried out by coupling amino acids to the nascent peptide chain in an amount between 1 and 1.5 equivalents.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

The terminology used herein is not intended to limit the scope of the invention. Throughout the text, including the appended claims, the singular forms "a," "an," and "the" include plural reference unless the context clearly dictates otherwise. Thus, for example, a reference to "an amino acid residue" is a reference to one or more amino acid residues and includes equivalents thereof known to those skilled in the art. In this invention, certain terms are used frequently, the meanings of which are provided herein. Unless defined otherwise, terms used herein have the same meaning as commonly understood to one of ordinary skill in the art in this field of technology. Some terms may also be explained in greater detail later in the specification.

The present invention is directed to methods for improving the synthesis of T-1249 and T-1249 counterparts, and in particular for improving aspects of the synthesis relating to solid phase synthesis of T-1249 peptide intermediate fragments. The methodology of the present invention is useful for making the T-1249 peptide and counterparts thereof using only two solid phase-synthesized peptide fragments. While the invention is generally directed at T-1249 synthesis, the inventive teachings herein can also be applicable to the synthesis of other peptides, particularly those that are synthesized using a combination of solid phase and solution phase approaches. The invention is also applicable to the synthesis of peptide intermediate fragments associated with impurities, particularly pyroglutamate impurities.

The methods described herein are particularly suitable for improving aspects of the scaled-up synthesis T-1249 peptides. Scaled-up procedures are typically performed to provide an amount of peptide useful for distribution. For example the amount of peptide in a scaled-up procedure can be 500 g, or 1 kg per batch or more, and more typically tens of kg to hundreds of kg per batch or more. In scaled-up synthetic procedures such as large-scale synthesis one or more large reaction vessels can be used. These can accommodate quantities of reagents such as resins, solvents, amino acids, and chemicals for various steps in the synthesis process, in a size that allows for production of peptides in amounts, for example, in the range of 100-500 kilograms or more.

The methods described herein are particularly suitable for improving aspects of the peptide synthesis, particularly for scaled-up procedures. In preferred embodiments, the inventive methods can provide such improvements as reduction in processing (synthesis) time, improvements in the yield of products, improvements in product purity, and reduction in amount of reagents and starting materials required.

The T-1249 peptide has the 39 amino acid sequence (reading from acetyl terminus (corresponding to the amino terminus) to the amide terminus (corresponding to the carboxy terminus)

```
Acetyl-WQEWEQKITALLEQAQIQQEKNEYELQ (SEQ. ID NO.1)
KLDKWASLWEWF-NH₂
```

Representative peptide fragments of T-1249 peptide include, but are not limited to, those having amino acid sequences as depicted in Table 1 below as well as counterparts of these. For example, in the table, the amino acid in the 39$^{th}$ position, which is F, may have a carboxylic acid terminus as in the case of the prime metabolite, or it may be modified as the amide in the case of the T-1249 peptide itself.

T-1249 is an anti-retroviral drug used for the treatment of HIV-1 infection. T-1249 functions to block fusion of the HIV-1 viral particle with host cells by blocking the conformational changes required for membrane fusion. Peptides having this type of activity are herein referred to as having T-1249 activity.

T-1249 synthesis typically utilizes both solid and liquid phase procedures to synthesize and combine groups of specific peptide fragments to yield the T-1249 product The T-1249 peptide and methods of making the T-1249 peptide and fragments thereof are described in U.S. Pat. No. 6,469, 136, incorporated herein by reference in its entirety.

The invention is also applicable to the synthesis of T-1249 counterparts, including full length T-1249 counterparts and T-1249 peptide intermediate counterparts. As used herein, a "T-1249 counterpart" refers to a compound derived from T-1249 or a T-1249 intermediate fragment. Peptide counterparts include but are not limited to peptide analogs, peptide derivatives, fusion compounds, and the like. Therefore, when referring to T-1249 peptide intermediate fragments having the sequences SEQ ID NO:2 and SEQ ID NO:3, their counterparts include, for example, peptide analogs, peptide derivatives, fusion compounds of SEQ ID NO:2 and SEQ ID NO:3, respectively.

As used herein, a peptide analog generally refers to a peptide having a modified amino acid sequence such as by one or more amino acid substitutions, deletions, inversions, and/or additions relative to another peptide or peptide counterpart. Substitutions preferably may be conservative or highly conservative. A conservative substitution refers to the substitution of an amino acid with another that has generally the same net electronic charge and generally the same size and shape. For instance, amino acids with aliphatic or substituted aliphatic amino acid side chains have approximately the same size when the total number carbon and heteroatoms in their side chains differs by no more than about four. They have approximately the same shape when the number of branches in the their side chains differs by no more than about one or two. Amino acids with phenyl or substituted phenyl groups in their side chains are considered to have about the same size and shape. Listed below are five groups of amino acids. Replacing an amino acid in a compound with another amino acid from the same groups generally results in a conservative substitution.

Group I: glycine, alanine, valine, leucine, isoleucine, serine, threonine, cysteine, methionine and non-naturally occurring amino acids with $C_1$-$C_4$ aliphatic or $C_1$-$C_4$ hydroxyl substituted aliphatic side chains (straight chained or monobranched).

Group II: glutamic acid, aspartic acid and nonnaturally occurring amino acids with carboxylic acid substituted $C_1$-$C_4$ aliphatic side chains (unbranched or one branch point).

Group III: lysine, ornithine, arginine and nonnaturally occurring amino acids with amine or guanidino substituted $C_1$-$C_4$ aliphatic side chains (unbranched or one branch point).

Group IV: glutamine, asparagine and non-naturally occurring amino acids with amide substituted $C_1$-$C_4$ aliphatic side chains (unbranched or one branch point).

Group V: phenylalanine, phenylglycine, tyrosine and tryptophan.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in the their side chains. Examples of highly conservative substitutions include valine for leucine, threonine for serine, aspartic acid for glutamic acid and phenylglycine for phenylalanine.

A peptide derivative generally refers to a peptide, a peptide analog, or other peptide counterpart having chemical modification of one or more of its side groups, alpha carbon atoms, terminal amino groups, and/or terminal carboxyl acid group. By way of example, a chemical modification includes, but is not limited to, adding chemical moieties, creating new bonds, and/or removing chemical moieties. Modifications at amino acid side groups include, without limitation, acylation of lysine e-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl (e.g., —CO-lower alkyl) modifications. Modifications of the terminal carboxy group include, without limitation, the amide, lower alkyl amide, dialkyl amide, and lower alkyl ester modifications. Thus, partially or wholly protected peptides constitute peptide derivatives.

Reference is made to the following set of peptides, which include T-1249 and T-1249 intermediate fragments, as set forth in Table 1.

TABLE 1

| SEQ ID NO: | Amino Acid Sequence | Corresponding Numbered Amino Acid Sequence of T-1249 |
|---|---|---|
| 1 | Ac-WQEWEQKITALLEQAQIQQE KNEYELQKLDKWASLWEWF | 1-39 |
| 2 | Ac-WQEWEQKITALLEQAQIQQE | 1-20 |
| 3 | KNEYELQKLDKWASLWEW | 21-38 |
| 4 | KNEYELQKLDKWASLWEWF | 21-39 |

To provide an overview, as based on the methods of the invention, the overall synthetic scheme for the T-1249 peptide is as follows. T-1249 (SEQ ID NO:1) is prepared by steps which include the solid phase synthesis of T-1249 peptide intermediate fragments Ac-WQEWEQKITALLEQAQIQQE (SEQ ID NO:2) and KNEYELQKLDKWASLWEW (SEQ ID NO:3). These peptides are synthesized using the methods described herein and then are cleaved from the solid phase resin in side-chain protected form. A phenylalaninamide residue is then coupled to the KNEYELQKLDKWASLWEW (SEQ ID NO:3) peptide intermediate in solution to produce KNEYELQKLDKWASLWEWF (SEQ ID NO:4). KNEYELQKLDKWASLWEWF (SEQ ID NO:4) is then coupled to Ac-WQEWEQKITALLEQAQIQQE (SEQ ID NO:2) in solution to produce Ac-WQEWEQKITALLEQA-QIQQEKNEYELQKLDKWASLWEWF (SEQ ID NO:1).

According to the present invention, solid phase synthesis techniques are used to prepare a first peptide fragment of T-1249 (Intermediate Fragment 1) having the 20 amino acid sequence of Ac-WQEWEQKITALLEQAQIQQE (SEQ ID NO:2) or a counterpart thereof. For reference with regard to a preferred method of solid phase synthesis, the amino-terminal glutamic acid (E) residue (i.e., residue number 20 of SEQ ID NO:2), which is present on the C-terminal portion of the peptide, is the first amino acid residue that is coupled to the solid phase resin and thus constitutes the alpha amino acid of the fragment in terms of its position with respect to the solid support resin. In this preferred method solid phase synthesis therefore proceeds by consecutively adding amino acid residues from the amino-terminus to the carboxyl terminus, sequentially adding amino acids in a manner corresponding to the desired sequence. The synthesis of the peptide intermediate fragment is complete after the N-terminal residue (for example, the N-terminal tryptophan (W) of SEQ ID NO:2) has been added to the nascent peptide chain.

Solid phase synthesis techniques are also used to prepare a second peptide fragment of T-1249 (Intermediate Fragment 2) having the 18 amino acid sequence of KNEYELQKLDK- WASLWEW (SEQ ID NO:3) or a counterpart thereof. For reference with regard to a preferred method of solid phase synthesis, the amino-terminal tryptophan (W) residue (i.e., residue number 18 of SEQ ID NO:3) is the first amino acid residue that is coupled to the solid phase resin and thus constitutes the alpha amino acid of the fragment in terms of its position with respect to the solid support resin. In this preferred method solid phase synthesis also proceeds by consecutively adding amino acid residues from the amino-terminus to the carboxyl terminus, sequentially adding amino acids in a manner corresponding to the desired sequence. The synthesis of the peptide intermediate fragment is complete after the N-terminal residue (for example, the N-terminal lysine (K) of SEQ ID NO:3) has been added to the nascent peptide chain.

Advantageously, neither Intermediate Fragment 1 nor Intermediate Fragment 2 includes an N-terminal glutamic acid (E) residue. To the extent that either intermediate fragment includes a glutamic acid residue, the residue either is positioned within the sequence or at the C-terminus of the intermediate fragment. It has been found that the purity of intermediate fragments can be significantly higher when using fragments having these general sequential arrangements of amino acids, inasmuch as a fragment with glutamic acid at the N-terminus tends to include more pyroglutamic acid impurities.

It is also noted that each of Intermediate Fragments 1 and 2 includes the residues of at least 18 amino acids. These are rather large peptide fragments in the context of solid phase synthesis, yet the principles of the present invention allow such large fragments and the resultant T-1249 to be synthesized with high yield and high purity.

According to the invention, it has been discovered by appropriately controlling the relative amount of peptide synthesized on the solid phase resin, advantageous effects can be obtained with regard to yield and purity of the peptide intermediate fragments. The relative amount of peptide synthesized can be controlled by the loading factor, which refers to the amount of the alpha amino acid coupled to an amount of resin, typically expressed as millimoles of alpha amino acid per gram of solid phase resin. For example, a loading factor of 0.25 would correspond to 25 mmol of alpha amino acid that is actually coupled to 100 g of solid phase resin. It is understood that the reaction coupling the first amino acid to the solid phase resin may not be completely efficient, and therefore the actual amount that is coupled may be less than a theoretical amount based on 100% coupling efficiency and the amounts of starting reagents. The actual amount of coupled material can be determined after the reaction has taken place. In order to determine the actual coupling, the peptide can be cleaved from the resin and assayed by using, for example, HPLC analysis versus a standard. Methods for determining the actual amount of coupled first amino acid residue are described herein.

According to the invention, it has been found that yield and purity of a relatively long peptide fragment (such as the peptide intermediate fragments SEQ ID NO:2 and SEQ ID NO:3 sequences) and hence the yield and purity of the resultant T-1249 peptide, tends to be higher at relatively lower loading factors, such as 0.5 or less. However, if the loading factor is, for example, lower than 0.2, then the product throughput may be curtailed. Balancing these concerns, the loading factor with respect to at least one of Fragments 1 and 2, preferably both Fragments 1 and 2, is between about 0.2 and about 0.50, preferably in the range of about 0.2 to about 0.45, and more preferably in the range of about 0.2 to about 0.40. For example, in one representative mode of practice, using a loading factor of about 0.34 would be suitable.

To illustrate this aspect, the following solid phase procedure can be performed. A suitable resin is obtained and prepared by washing in an appropriate solvent. Next, a solution containing the first amino acid in activatable and protected form is added to the washed resin. To achieve a loading factor within a desired range, the amount and/or concentration of amino acid, and/or other reaction factors, such as the presence and concentration of co-reagents such as HOBT, the duration of the coupling reaction, the temperature of the coupling reaction, and so forth can be chosen.

Solid phase synthesis using Fmoc chemistry can be used to prepare a T-1249 intermediate fragment(s) (such as peptide intermediate fragments that include SEQ ID NO:2 and SEQ ID NO:3) coupled to a resin. After the peptide intermediate fragment is synthesized on the resin, it cleaved using a cleavage reagent to generate a peptide intermediate fragment in solution that is in a protected form. The peptide intermediate fragment is then separated from the resin. In some cases the peptide intermediate fragment is contacted with a precipitating agent as a measure to purify the peptide intermediate fragment prior to performing solution phase coupling.

Methods for the synthesis of peptides using a solid-phase approach are well known in the art. Accordingly, the invention contemplates using any solid phase synthetic approach using a low loading factor for preparing a peptide intermediate fragments which can be used in the preparation of a T-1249 final product.

For example, the T-1249 peptide intermediate fragments described herein can be synthesized by SSPS techniques using standard Fmoc protocols. Fmoc protocols are described in, for example, Carpin et al. (1970), J. Am. Chem. Soc. 92(19):5748-5749; Carpin et al. (1972), J. Org. Chem. 37(22):3404-3409, "Fmoc Solid Phase Peptide Synthesis," Weng C. Chan and Peter D. White Eds. (2000) Oxford University Press Oxford Eng.

Any type of support suitable in the practice of solid phase peptide synthesis can be used. In preferred embodiments, the support comprises a resin that can be made from one or more polymers, copolymers or combinations of polymers such as polyamide, polysulfamide, substituted polyethylenes, polyethyleneglycol, phenolic resins, polysaccharides, or polystyrene. The polymer support can also be any solid that is sufficiently insoluble and inert to solvents used in peptide synthesis. The solid support typically includes a linking moiety to which the growing peptide is coupled during synthesis and which can be cleaved under desired conditions to release the peptide from the support. Suitable solid supports can have linkers that are photo-cleavable, TFA-cleavable, HF-cleavable, fluoride ion-cleavable, reductively-cleavable; Pd(0)-cleavable; nucleophilically-cleavable; or radically-cleavable. Preferred linking moieties are cleavable under conditions such that the cleaved peptide is still substantially globally protected.

In one preferred method of synthesis, the peptide intermediate fragments synthesized on an acid sensitive solid support that includes trityl groups, and more preferably on a resin that includes trityl groups having pendent chlorine groups, for example a 2-chlorotrityl chloride (2-CTC) resin (Barlos et al. (1989) Tetrahedron Letters 30(30):3943-3946). Examples also include trityl chloride resin, 4-methyltrityl chloride resin, 4-methoxytrityl chloride resin, 4-aminobutan-1-ol 2-chlorotrityl resin, 4-aminomethylbenzoyl 2-chlorotrityl resin, 3-aminopropan-1-ol 2-chlorotrityl resin, bromoacetic acid 2-chlorotrityl resin, cyanoacetic acid 2-chlorotrityl resin, 4-cyanobenzoic acid 2-chlorotrityl resin, glicinol 2-chlorotrityl resin, propionic 2-chlorotrityl resin, ethyleneglycol 2-chlorotrityl resin, N-Fmoc hydroxylamine 2-chlorotrityl resin, hydrazine 2-chlorotrityl resin. Some preferred solid supports include polystyrene, which can be copolymerized with divinylbenzene, to form support material to which the reactive groups are anchored.

Peptide material typically is attached to the resin beads both at the bead surfaces and within the bead interiors. Fmoc and side chain protected peptide is readily cleaved in a protected state from this resin using mildly acidic reagents such as dilute TFA in DCM or acetic acid.

Other resins that are used in solid phase synthesis include "Wang" resins, which comprise a copolymer of styrene and divinylbenzene with 4-hydroxymethylphenyloxymethyl anchoring groups (Wang, S. S. 1973, J. Am. Chem. Soc.), and 4-hydroxymethyl-3-methoxyphenoxybutyric acid resin (Richter et al. (1994), Tetrahedron Letters 35(27):4705-4706). The Wang, 2-chlorotrityl chloride, and 4-hydroxymethyl-3-methoxyphenoxy butyric acid resins can be purchased from, for example, Calbiochem-Novabiochem Corp., San Diego, Calif.

In order to provide a support having a first coupled amino acid, the resin can be prepared, by example, washing, and then incubated with a solution containing an activated, protected amino acid. The first amino acid and subsequent amino acids that are coupled to the resin typically include an N-terminal protecting group, a side chain protecting group (depending on the specific amino acid), and a group that is reactive with a group pendant from the resin, or a group that is reactive with the pendent amino acid.

In preferred aspects, the first amino acid is attached to the support at the carboxy end, while the N-terminus and side chain groups are protected, as appropriate, by protecting groups. As exemplary description, solid phase synthesis of the Ac-WQEWEQKITALLEQAQIQQE (SEQ ID NO:2) peptide intermediate fragment is carried from the carboxy-terminal to $NH_2$ terminal direction by first loading a protected glutamic acid residue onto a 2-chlorotritylchloride (2-CTC) resin.

The nature and use of protecting groups is well known in the art. Generally, a suitable protecting group is any sort of group that that can help prevent the atom or moiety to which it is attached, e.g., oxygen or nitrogen, from participating in undesired reactions during processing and synthesis. Protecting groups include side chain protecting groups and amino- or N-terminal protecting groups. Protecting groups can also prevent reaction or bonding of carboxylic acids, thiols and the like.

A side chain protecting group refers to a chemical moiety coupled to the side chain (i.e., R group in the general amino acid formula $H_2N$—C(R)(H)—COOH) of an amino acid that helps to prevent a portion of the side chain from reacting with chemicals used in steps of peptide synthesis, processing, etc. The choice of a side chain-protecting group can depend on various factors, for example, type of synthesis performed, processing to which the peptide will be subjected, and the desired intermediate product or final product. The nature of the side chain protecting group also depends on the nature of the amino acid itself. Generally, a side chain protecting group is chosen that is not removed during deprotection of the α-amino groups during the solid phase synthesis. Therefore the α-amino protecting group and the side chain protecting group are typically not the same.

In some cases, and depending on the type of reagents used in solid phase synthesis and other peptide processing, an amino acid may not require the presence of a side-chain protecting group. Such amino acids typically do not include a reactive oxygen, nitrogen, or other reactive moiety in the side chain.

Examples of side chain protecting groups include acetyl (Ac), benzoyl(Bz), tert-butyl, triphenylmethyl(trityl), tetrahydropyranyl, benzyl ether(Bzl) and 2,6-dichlorobenzyl (DCB), t-butoxycarbonyl (BOC), nitro, p-toluenesulfonyl (Tos), adamantyloxycarbonyl, xanthyl(Xan), benzyl, 2,6-dichlorobenzyl, methyl, ethyl and t-butyl ester, benzyloxycarbonyl(Z), 2-chlorobenzyloxycarbonyl(2-Cl-Z), Tos, t-amyloxycarbonyl(Aoc), and aromatic or aliphatic urethan-type protecting groups. photolabile groups such as nitro veritryl oxycarbonyl (NVOC); and fluoride labile groups such as trimethylsilyl oxycarbonyl (TEOC).

Preferred side chain protecting groups include t-Bu group for Tyr(Y), Thr(T), Ser(S) and Asp(D) amino acid residues; the trt group for His(H), Gln(O) and Asn(N) amino acid residues; and the Boc group for Lys(K) and Trp(W) amino acid residues.

For example, any one or more of the side-chains of the amino acid residues of peptide fragments listed in Table 1 may be protected with standard protecting groups such as t-butyl (t-Bu), trityl (trt) and t-butyloxycarbonyl (Boc). The t-Bu group is the preferred side-chain protecting group for amino acid residues Tyr(Y), Thr(T), Ser(S) and Asp(D); the trt group is the preferred side-chain protecting group for amino acid residues His(H), Gln(O) and Asn(N); and the Boc group is the preferred side-chain protecting group for amino acid residues Lys(K) and Trp(W).

Preferably, all the asparagine residues of each peptide fragment of the invention are protected. In addition, it is preferred that the tryptophan residue is protected with a Boc group.

An amino-terminal protecting group includes a chemical moiety coupled to the alpha amino group of an amino acid. Typically, the amino-terminal protecting group is removed in a deprotection reaction prior to the addition of the next amino acid to be added to the growing peptide chain, but can be maintained when the peptide is cleaved from the support. The choice of an amino terminal protecting group can depend on various factors, for example, type of synthesis performed and the desired intermediate product or final product.

Examples of amino-terminal protecting groups include (1) acyl-type protecting groups, such as formyl, acrylyl(Acr), benzoyl(Bz) and acetyl(Ac); (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as 9-fluorenyl-methyloxycarbonyl (Fmoc), cyclopentyloxycarbonyl, adamantyloxycarbonyl, and cyclohexyloxycarbonyl; and (5) thiourethan-type protecting groups, such as phenylthiocarbonyl. Preferred protecting groups include 9-fluorenyl-methyloxycarbonyl (Fmoc), 2-(4-biphenylyl)-propyl(2)oxycarbonyl(Bpoc), 2-phenylpropyl(2)-oxycarbonyl (Poc) and t-butyloxycarbonyl (Boc).

According to the invention, the protecting groups are typically retained on the peptide intermediate fragments throughout solid phase synthesis and also into and throughout the solution phase coupling reaction. (Generally, after a solution phase coupling step is completed, a deprotection step is performed to remove one or more protecting groups from the peptide.)

Specific examples of first amino acids having specific protecting groups that can be coupled to the resin for the synthesis of peptide intermediate fragments having SEQ ID NO:2 and SEQ ID NO:3, can be FmocGlu(OtBu)OH and FmocTrp (Boc)OH, respectively.

In order to prepare a resin for solid phase synthesis, the resin can be pre-washed in a solvent. For example, a solid phase resin such as a 2-CTC resin is added to a peptide chamber and pre-washed with a suitable solvent. The washing can be performed to prepare the resin for contact with the first amino acid to be coupled to the resin. In essence, a pre-wash can be performed to promote efficient coupling of the first amino acid to the resin. The pre-wash solvent may be chosen based on the type of solvent (or mixture of solvents) that is used in the coupling reaction, or vice versa.

Solvents that are suitable for washing, and also the subsequent coupling reaction include dichloromethane (DCM), dichloroethane (DCE), dimethylformamide (DMF), methylene chloride, and the like, as well as mixtures of these reagents. Other useful solvents include DMSO, pyridine, chloroform, dioxane, tetrahydrofuran, ethyl acetate, N-methylpyrrolidone, and mixtures thereof. In some cases coupling can be performed in a binary solvent system, such as a mixture of DMF and DCM.

As described herein, it is desired to control the loading factor of the first alpha amino acid on the resin to be in the range of about 0.2 to about 0.50, preferably about 0.2 to about 0.45, and more preferably about 0.2 to about 0.40. Therefore, a solution is prepared having an amount of amino acid that will provide a coupling factor in the target range. This can be determined knowing generally, what the coupling efficiency is for a particular reaction. For example, when it is desired to have a target loading factor of about 0.34, and if it is known that the coupling efficiency is about 80%, then a coupling solution containing 0.425 mmol of amino acid for every gram of resin should be used (0.34/0.8).

The coupling reaction can be performed in the presence of one or more compounds that enhance or improve the coupling reaction. Compounds that can increase the rate of reaction and reduce the rate of side reactions include phosphonium and uronium salts that can, in the presence of a tertiary base, for example, diisopropylethylamine (DIEA) and triethylamine (TEA), convert protected amino acids into activated species (for example, BOP, PyBOPO, HBTU, and TBTU all generate HOBt esters). Other reagents help prevent racemization by providing a protecting reagent. These reagents include carbodiimides (for example, DCC or WSCDI) with an added auxiliary nucleophile (for example, 1-hydroxy-benzotriazole (HOBt), 1-hydroxy-azabenzotriazole (HOAt), or HOSu). Another reagent that can be utilized is TBTU. The mixed anhydride method, using isobutyl chloroformate, with or without an added auxiliary nucleophile, is also utilized, as is the azide method, due to the low racemization associated with it. These types of compounds can also increase the rate of carbodiimide-mediated couplings, as well as prevent dehydration of Asn and Gln residues.

Coupling completion can be monitored with a qualitative ninhydrin test as described herein. After the coupling is determined to be complete, the coupling reaction mixture is washed with a solvent, and the coupling cycle is repeated for each of the subsequent amino acid residues of the peptide material. Following the final coupling cycle, the resin is washed with a solvent such as NMP, and then washed with an inert second solvent such as DCM.

In order to couple the next amino acid, removal of the N-terminal protecting group (for example, an Fmoc group) is typically accomplished by treatment with a reagent that includes 20-50% (on a weight basis) piperidine in a solvent, such as N-methylpyrrolidone (NMP) or dimethylformamide (DMF). After removal of the Fmoc protecting group, several washes are typically performed to remove residual piperidine and Fmoc by-products (such as dibenzofulvene and its piperidine adduct).

After the first amino acid has been coupled to the resin at a desired loading factor and the N-terminal protecting group has been removed, subsequent amino acids can be added to prepare the peptide intermediate fragments. The subsequent amino acids can be utilized at a stoichiometric excess of amino acids in relation to the loading factor. However, it has been found that the solid phase synthesis of the specific T-1249 intermediate fragments described herein does not require a great excess of amino acids (and corresponding reagents) to be used in the solid phase synthesis of these fragments. Generally, the amount of amino acids used in the coupling step is at least equivalent to the loading factor of the first amino acid on the resin (1 equivalent or more). Preferably the amount of amino acids used in the coupling step is 1.3 equivalent (0.3 excess) or more, and most preferably about 1.5 equivalent (0.5 excess). In some cases, for example, the coupling step utilizes an amount equivalent of amino acids in the range between 1 and 1.5 (greater than 1 and less than 1.5).

It has been found that this excess of amino acids (e.g., about 1.5) is sufficient for the coupling reaction to go to completion. This excess can also help the reaction tolerate excess base from the deprotection reagent.

The steps of coupling, washing, N-terminal deprotecting group deprotecting, and washing can be repeated until the desired T-1249 intermediate product is formed.

Following solid phase synthesis and in order to remove the T-1249 intermediate peptides from the resin, a cleaving treatment is carried out in a manner such that the cleaved T-1249 intermediate peptides still bear sufficient side chain and terminus protecting groups. Leaving the protective groups in place helps to prevent undesirable coupling or other undesirable reactions of peptide fragments during or after cleaving. In the case when FMOC or similar chemistry is used to synthesize the peptide, protected cleaving may be accomplished in any desired fashion such as by using a relatively weak acid reagent such as acetic acid or dilute TFA in a solvent such as DCM, which can also swell the resin, being useful for cleavage and separation process. The use of 0.5 to 10 weight percent, preferably 1 to 3 weight percent TFA in DCM is preferred. See, e.g., U.S. Pat. No. 6,281,335.

Steps of cleaving the peptide intermediate fragment from the solid phase resin can proceed along the lines of the exemplary process as follows. However, any suitable process that effectively cleaves the peptide intermediate fragment from the resin can be used. For example, approximately 5 to 20, preferably about 10 volumes of a solvent containing an acidic cleaving reagent is added to the vessel. The resin beads are immersed in the reagent as a consequence. The cleaving reaction occurs as the liquid contents are agitated at a suitable temperature for a suitable time period. Agitation helps prevent the beads from clumping. Suitable time and temperature conditions will depend upon factors such as the acid reagent being used, the nature of the peptide, the nature of the resin, and the like. As general guidelines, stirring at from about −15° C. to about 5° C., preferably from about −10° C. to about 0° C. for about 5 minutes to two hours, preferably about 25 minutes to about 45 minutes would be suitable. Cleaving time may be in the range of from about 10 minutes to about 2 hours. For large-scale production, a preferred time is in the range of from about 15 to 50 minutes. Cleaving is desirably carried out in such chilled temperature range to accommodate a reaction exotherm that might typically occur during the reaction. In addition, the lower temperature of the cleavage reaction prevents acid sensitive side chain protecting groups, such as trt groups, from being removed at this stage.

At the end of the cleaving treatment, the reaction is quenched. This may be achieved, for example, by adding a suitable base, such as pyridine or the like, to the vessel, and continuing to agitate and stir for an additional period such as for an additional 5 minutes to 2 hours, preferably about 20 minutes to about 40 minutes. Adding the base and continued agitation causes the temperature of the vessel contents to increase. At the end of agitation, the vessel contents may be at a temperature in the range of from about 0° C. to about 15° C., preferably about 5° C. to about 10° C.

Factors such as swelling and shrinking the resin in order to improve aspects of the peptide recovery can optionally be incorporated into the overall synthesis process.

For example, after cleaving, the support can optionally be washed one or more times with a swelling reagent to extract cleaved peptide into the resultant wash(es), and the wash(es) are collected to allow recovery of the peptide from those washes. For example, cleaving a peptide from the 2-CTC resin using dilute TFA in DCM would further constitute all or a portion of a swelling treatment. After cleaving, and after the swelling treatment is completed, the support can be subjected to one or more optional shrinking washes that allow additional amounts of peptide to be recovered from such shrinking washes as well as enhancing the ability to recover additional peptide from one or more subsequent optional swelling washes. The subsequent optional swelling wash(es), constituting an additional swelling treatment, can be carried out after the shrinking treatment is completed.

Because a swelling solvent such as DCM may be used as a constituent in the cleaving reagent, the cleaving treatment also may constitute a first swelling treatment in which a significant amount of cleaved peptide will be extracted into the liquid. When swelled with TFA in DCM, the bead volume will tend to be largest at the onset of the cleaving treatment. The beads will still be swelled, but their volume decreases, as peptide is extracted into the liquid.

After quenching, the vessel contents are emptied and collected to recover the peptide extracted into the wash. Pressure may be used to force the liquid mixture containing peptide material carried by the liquid through the filter and out of the vessel. The beads remaining in the vessel will still contain residual DCM and will still be swelled to some extent. A significant amount of residual peptide also tends to be retained in the beads, and the subsequent shrinking and swelling treatments help to recover significant portions of the residual peptide.

As an option, it may be desirable to wash the collected cleaving reagent with water prior to concentration via distillation or the like, usually after some concentration has been accomplished except. Water washing after cleaving is believed to be useful to enhance peptide quality and, therefore, to some extent yield. Water washing is believed to be helpful in removing residual TFA and its byproducts. After the water wash/extraction treatment, the liquid mixture may be transferred to a distillation apparatus, where the mixture is concentrated further by removing, for example, the DCM or the like.

After the cleaving mixture is emptied from the vessel and collected for peptide recovery, the vessel contents may be subjected to one or more additional swelling washes into which additional peptide may be extracted and then recovered. These additional swelling washes also help to wash the vessel and remove residual cleaving reagents and by-products. Such ingredients are desirably removed prior to proceeding with a shrinking treatment so that the shrinking liquid will not react with them. For instance, it is desirable to remove TFA from the vessel before adding a shrinking liquid containing ethanol inasmuch as ethanol can react with TFA. A typical swelling wash treatment may occur with agitation for a time period of from about 2 minutes to 2 hours, preferably from about 10 minutes to about 50 minutes. After the wash is done, the wash is removed from the vessel and then may be added to the distillation vessel with the other swelling washes. Optionally, prior to being added to the distillation pot, these additional swelling washes, if any, may be subjected to a water extraction treatment to remove impurities.

In some aspects, the peptide intermediate fragments can be prepared for solution phase coupling by performing step to enhance their purity, for example, by crystallization. One or more of the T-1249 peptide intermediate fragments can be treated with a solution containing IPA, such as a mixture of IPA and DCM, or IPA and water, to crystallize the peptide intermediate fragments.

After solid phase synthesis, cleavage from the resin, and any washing or purification of the peptide intermediate, the peptide intermediate fragment having the sequence KNEYELQKLDKWASLWEW (SEQ ID NO:3) is reacted with a phenylalaninamide (F—$NH_2$) residue to produce a peptide intermediate fragment having the sequence KNEYELQKLDKWASLWEWF (SEQ ID NO:4). This solution phase reaction can be performed in a suitable solution phase reaction solution, as described herein. This peptide intermediate product can be precipitated in a nonsolvent, for example, water, and washed to improve purity.

The T-1249 side chain-protected peptide intermediate fragments Ac-WQEWEQKITALLEQAQIQQE (SEQ ID NO:2) and KNEYELQKLDKWASLWEWF (SEQ ID NO:4) are coupled together in solution to form a full-length T-1249 peptide having the sequence Ac-WQEWEQKITALLEQA-QIQQEKNEYELQKLDKWASLWEWF (SEQ ID NO:1). These peptide intermediate fragments chemically arranged wherein the N-terminus of the KNEYELQKLDKWASL-WEWF peptide intermediate fragment is coupled to the C-terminus of the Ac-WQEWEQKITALLEQAQIQQE peptide fragment.

Preferably, the peptides are supplied to the coupling reaction at a purity level of 80% or greater, or more preferably 82.5%, and most preferably 85% or greater based on a HPLC profile. According to the methods of the invention, the solid phase synthesis utilizing a low loading factor is a significant aspect for preparing the T-1249 intermediate peptide fragments having a higher purity level.

Peptide coupling reactions are reviewed in, for example, *New Trends in Peptide Coupling Reagents*; Albericio, Fernando; Chinchilla, Rafeal; Dodsworth, David J.; and Najera, Armen; Organic Preparations and Procedures International (2003), 33(3), 203-303.

Coupling of peptide intermediate fragments can be carried out using in situ coupling reagents, for example, BOP, o-(benzotriazol-1-yl)-N,N,N',N'-tetramethyluronium hexafluorophosphate (HBTU), HATU, dicyclohexylcarbodiimide (DCC), water-soluble carbodiimide (WSCDI), or o-(benzotriazol-1-yl)-N,N,N',N'-tetramethyluronium tetrafluoroborate (TBTU). Other coupling techniques use preformed active esters such as hydroxysuccinimide (HOSu) and p-nitrophenol (HONp) esters; preformed symmetrical anhydrides; N-carboxyanhydrides (NCAs); or acid halides such as acyl fluoride as well as acyl chloride.

A suitable coupling solvent can be used in the coupling reaction. It is understood that the coupling solvent(s) used can affect the degree of racemization of the peptide bond formed; the solubility of the peptide and/or peptide fragments; and the coupling reaction rate.

In some embodiments, the coupling reaction includes a water-miscible solvent(s). Examples of water-miscible solvents include, for example, DMSO, pyridine, chloroform, dioxane, tetrahydrofuran, ethyl acetate, N-methylpyrrolidone, dimethylformamide, dioxane, or mixtures thereof.

In other embodiments, the coupling reaction includes a non water-miscible solvent. An exemplary non water-miscible solvent is methylene chloride. In these embodiments, the non water-miscible solvent is preferably compatible with the deprotection reaction; for example, if a non water-miscible solvent is used preferably it does not adversely affect the deprotection reaction.

After the peptide intermediate fragments have been coupled to produce a T-1249 peptide, the product can be subject to a deprotection step to remove the side chain protecting groups.

The removal of side chain protecting groups by global deprotection typically utilizes a deprotection solution that includes an acidolytic agent to cleave the side chain protecting groups. Commonly used acidolytic reagents for global deprotection include neat trifluoroacetic acid (TFA), HCl, lewis acids such as $BF_3Et_2O$ or $Me_3SiBr$, liquid hydrofluoric acid (HF), hydrogen bromide (HBr), trifluoromethane sulfuric acid, and combinations thereof. The deprotection solution also includes one or more suitable cation scavengers, for example, dithiothreitol, anisole, p-cresol, ethanedithiol, or dimethyl sulfide. The deprotection solution can also include water. As used herein, amounts of reagents present in the deprotection composition are typically expressed in a ratio, wherein the amount of an individual component is expressed as a numerator in "parts", such as "parts weight" or "parts volume" and the denominator is the total parts in the composition. For example, a deprotection solution containing TFA:$H_2O$:DTT in a ratio of 90:5:5 (weight/weight/weight) has TFA at 90/100 parts by weight, $H_2O$ at 5/100 parts by weight, and DTT at 5/100 parts by weight.

In some embodiments, the deprotection reaction can be performed wherein the amount of the acidolytic agent, preferably TFA, in the deprotection composition is greater than 90/100 parts by weight. Other preferred deprotection compositions include an amount of acidolytic agent in an amount of 93/100 parts by weight or greater, or in an amount in the range of 93/100 by weight to 95/100 parts by weight.

After the T-1249 peptide has been deprotected, and is in a final form, optionally the peptide batch can be subject to a procedure that deaggregates aggregated peptide that may be present at this stage in the overall synthetic scheme.

Deaggregation can be performed by dissolving peptide samples in aqueous base and then acidifying the aqueous mixture to precipitate the peptide in the presence of at least one of a salt and a co-solvent. Preferably, both a salt and co-solvent are present in the deaggregation solution. Deaggregation can be carried by precipitating the peptide relatively rapidly (at least in a first stage of acidifying in which the pH of the alkaline medium is reduced to a pH in the range of 6 to 7.5, after which acidification to a final desired pH, e.g., 3 to 6, can occur more slowly) at relatively low temperature.

For deaggregation, the aqueous, buffered, alkaline solution is generally derived from ingredients comprising water, at least one salt, and a sufficient amount of at least one base to provide the desired dissolution pH. The T-1249 peptide and various ingredients constituting the aqueous, buffered, alkaline solution may be combined in any order. In one mode of practice, the solution is prepared from its constituent ingredients and then the peptide is added to the already prepared solution. In another mode of practice, the peptide may be added to an aqueous solution comprising the salt wherein the solution has a pH that is too low for dissolution to occur. A base is then added to this mixture in order to raise the pH to a value at which dissolution will occur. As still yet another alternative, the salt may be added to the solution before, during, and/or after dissolution. Generally, though, the salt is incorporated into the solution before the pH is lowered in a manner to cause the peptide to precipitate as is described further below.

The concentration of the peptide in the solution may vary over a wide range. As general guidelines, the T-1249 peptide concentration in the solution may be in the range of from about 3 g/L to about 6 g/L.

A variety of one or more bases may be incorporated into the solution to provide the desired pH. Representative examples of suitable bases include hydroxide bases such as NaOH and bicarbonate and carbonate bases such as sodium or potassium bicarbonate or sodium or potassium carbonate. Sodium hydroxide is preferred, especially 0.5 N to 1 N NaOH. The base is used to adjust the pH to a desired value at which the peptide will dissolve in the solution in a reasonable amount of time. For many peptides, this corresponds to a dissolution pH in the range of from about 8 to about 11.

The salt constituent(s) of the solution improve the dissolution characteristics of the resulting precipitated peptide. Specifically, a soluble peptide that dissolves readily in aqueous solution at lower pH is prepared more consistently when a salt is present at an appropriate concentration.

A variety of salts would be useful in the practice of the present invention. Examples include sodium carbonate, sodium acetate, ammonium carbonate, ammonium acetate, sodium bicarbonate, ammonium bicarbonate, sodium and potassium versions of these, combinations of these, and the like. Ammonium acetate is most preferred.

The concentration of the salt in the solution may vary over a wide range. Using 1 to 200 mM equivalents of salt is one example of a salt concentration range that would be suitable. In a specific mode of practice, using about 5 mM to about 50 mM, more preferably about 10 mM equivalents of salt, especially ammonium acetate, has been found to be suitable.

The dissolution temperature(s) generally refers to the temperature(s) of the aqueous, solution in which the peptide is dissolved. Dissolution may occur at any suitable temperature. Generally, dissolving the peptide in a solution maintained at one or more temperatures in a range from about 10° C. to about 30° C., preferably about 10° C. to about 25° C., more preferably about 15° C. to about 20° C. would be preferable.

A co-solvent is preferably incorporated into the solution so that subsequent precipitation of the peptide occurs in the presence of the co-solvent. The co-solvent can be added to the solution before, during, and or after dissolution, but preferably is added promptly after dissolution of the peptide. The co-solvent refers to one or more additional solvents in which the peptide is soluble at the dissolution pH. Preferably, the peptide is also soluble in the co-solvent at 25° C. and physiological pH when the peptide is sufficiently deaggregated that ratio of the measured molecular weight of the peptide to the theoretical molecular weight of the peptide is in the range from about 2:1 to about 1:1. Examples of co-solvents include acetonitrile, methanol, combinations of these, and the like.

In preferred embodiments of the invention, a sufficient amount of co-solvent is added to the solution such that the solution contains from about 2 to 50 volume percent, preferably from about 5 to about 30 volume percent, and more preferably from about 10 to about 20 volume percent of the co-solvent.

After dissolution, and desirably after addition of the co-solvent, the pH of the solution optionally further is increased by adding additional base in order to facilitate further deaggregation of the peptide, if desired. The solution is then desirably promptly filtered. Pressure filtering through a 0.2 micron filter would be suitable. The filtrate is optionally degassed under vacuum, after which the solution may be aged for a suitable time period before further processing in order to complete the deaggregation process. Generally, aging so that the total time that the peptide is at the elevated pH (including not just aging time, but also filtering time, degassing time, etc.) is in the range of from about 5 minutes to about 6 hours, more preferably about 30 minutes to about 2 hours. After aging, the solution optionally may be filtered again.

After aging, the pH of the solution is reduced, e.g., acidified, under conditions effective to cause the peptide to precipitate. As general guidelines, a final pH in the range of from about 3 to about 6, preferably 4 to about 6 could be suitable. As a specific example, a final pH of 5.3 to 5.5 is desirable with respect to the T-1249 peptide.

The pH of the solution preferably is lowered by adding one or more acids to the solution. Examples of acids include HCl, sulfuric acid, acetic acid, oxalic acid, combinations of these, and the like. Acetic acid is preferred. For instance, aqueous, 5% or 10% acetic acid solution have been found to be suitable.

In some modes of practice, peptide product with excellent dissolution properties can still be obtained if the acid is added relatively rapidly to lower the pH only to an intermediate pH. After this initial, relatively rapid addition of acid, acid is added at a second, relatively slower rate to lower the pH of the solution to the final desired pH. Suitable intermediate pH values would be in the range of from about 6 to about 8, more preferably from about 6.0 to about 7.5. Desirably, the initial rapid lowering of the pH occurs in a time period of less than about one hour, preferably 30 minutes or less, more preferably 15 minutes or less.

For example, one suitable mode of practice involves lowering the pH of a T-1249 solution initially at a pH of 11. A sufficient amount of acid is added relatively rapidly over a period of 10 minutes to lower the pH to an intermediate value of about 6.0. Then, acid is added more slowly over 10 to 20 minutes to lower the pH to 5.3 to 5.5.

The mixture is desirably mixed well during the course of adding the acid to cause precipitation of the peptide. As general guidelines, it is preferred to agitate the mixture while adding the acid as vigorously as is practical while leaving a sufficient safety margin to avoid foaming the mixture.

The addition of acid to cause precipitation of the peptide may be carried out with the solution at any suitable temperature. As guidelines, carrying out precipitation at a temperature in the range of 10° C. to 30° C., preferably 15° C. to 25° C., most preferably 16° C. to 18° C. would be suitable.

After precipitation, the peptide is desirably isolated and dried before being combined with other ingredients, lyophilized, packaged, stored, further processed, and/or otherwise handled. This may be accomplished in any suitable fashion. According to one suitable approach, the peptide is collected via filtering, washed with ample water washes to reduce final salt content to a suitable level, and then dried.

If the peptide precipitates in an unsuitable form for filtration (for example if the precipitate is "gel like"), the precipitate can be subjected to an aging process with desirable agitation in which the peptide particles are agglomerated to "harden" the particles.

In a preferred mode of practice, this age-hardening treatment involves aging the peptide with agitation in the course of a cooling/heating/cooling treatment. This improves the filtering characteristics of the peptide without undue damage of the peptide tertiary structure. In a specific mode of practice, the treatment involved aging the particles in aqueous mixture for 5 minutes to 48 hours, preferably 30 minutes to 8 hours, more preferably 30 minutes to 2 hours at a first temperature below ambient temperature preferably being in the range of from more than 0° C. to about 20° C., preferably 10° C. to 20° C., more preferably about 16° C. Agitation desirably is used to ensure that the particles are well dispersed during the aging.

Next, the temperature of the mixture is increased by about 2° C. to about 30° C., preferably about 5° C. to about 15° C. to a moderately warmer temperature, wherein the transition to the warmer temperature occurs with agitation over a period of from about 1 minute to about 48 hours, preferably 5 minutes to 8 hours, more preferably 20 minutes to 2 hours. Preferably, the new, moderately warmer temperature is still at ambient or below. In a specific mode of practice, increasing the temperature from 16° C. to 21° C. in about one hour was found to be suitable. Agitation desirably continues during this transition. The mixture is then aged at the warmer temperature for a period of from 5 minutes to 8 hours, preferably 20 minutes to 4 hours, more preferably about 3 hours, with agitation.

After this aging step, the temperature of the mixture is lowered by about 2° C. to about 30° C., preferably about 5° C. to about 15° C. to a moderately cooler temperature, wherein the transition to the cooler temperature preferably occurs with agitation over a period of from about 1 minute to about 48 hours, preferably 5 minutes to 8 hours, more preferably 20 minutes to 4 hours. Preferably, the new, moderately cooler temperature is in the range of from above about 3° C. to about 18° C., more preferably about 110° C. In a specific mode of practice, lowering the temperature from 21° C. to 10° C. in about two hours was found to be suitable. The mixture is then further aged at the cooler temperature preferably for a period of from about 5 minutes to 48 hours, more preferably about 6 hours.

This aging treatment improves the filtering characteristics of the precipitated particles in that filtering and separating the peptide particles from the filtrate occur more readily without unduly changing the secondary structure of the peptide Thus, after this aging, the precipitate is filtered, preferably pressure filtered such as with 1 psig $N_2$. The filter cake may be washed one or more times with water desirably pre-cooled such as to a temperature in the range of from about 3° C. to about 20° C., preferably 5° C. to about 15° C., more preferably about 10° C. This helps to lower the salt content of the cake. The filter cake may then be partly or wholly dried, such as by passing nitrogen through the cake with nitrogen at a suitable temperature for a suitable time period, such as 1 minute to 48 hours, preferably 5 minutes to 8 hours, more preferably about 6 hours. Using nitrogen that is at about ambient temperature is convenient and suitable. The cake may be periodically mixed to facilitate drying. Drying optionally may be completed in a separate drying apparatus. Such optional drying preferably occurs under vacuum, e.g., less than 30 mm Hg, at a moderate temperature so as not to degrade the peptide, e.g., at a temperature less than about 30° C., preferably less than about 28° C.

Methods that can be used for the preparation of T-20 peptide and fragments thereof are described in Assignee's U.S.

Provisional Application No. 60/640,312, filed Dec. 30, 2004, and titled METHODS AND COMPOSITIONS FOR PREPARING PEPTIDES WITH EXCELLENT SOLUBILITY CHARACTERISTICS IN AQUEOUS SOLUTION AT PHYSIOLOGICAL PH in the name of Ramakrishna V. Nalitham, the entirety of which is incorporated herein by reference; and in Assignee's U.S. Provisional Application No. 60/640,717 filed Dec. 30, 2004 and titled METHODS AND COMPOSITIONS FOR COLORIMETRICALLY ASSESSING PEPTIDE CHARACTERISTICS in the name of Ileana Isabel Nuiry, the entirety of which is incorporated herein by reference.

The principles of the present invention will now be further illustrated with respect to the following illustrative examples.

EXAMPLES

For the following examples, the following standard reagents and nomenclature are adopted:

Chloranil test: The chloranil test solution was prepared by adding a drop of a saturated solution of chloranil in toluene to about 1 ml of acetone. The NMP washings were tested by adding a drop of the washing to the chloranil test solution. A blue or violet color is a positive indication for the presence of secondary amine, indicating that Fmoc deprotected by-products and/or residual piperidine are still present.

Ninhydrin (Keiser) test: In the qualitative ninhydrin test, a 2-20 mg sample of the resin was withdrawn and washed with NMP and subsequently DCM or methanol. Three drops of a 76% solution of phenol in ethanol, six drops of a 0.2 mM KCN solution in pyridine, and three drops of a 0.28 M solution of ninhydrin in ethanol were added to the sample, and the sample was placed in a heating block at about 100° C. for about 5 minutes. The sample was removed and immediately diluted with an ethanol/water solution (9:1). A blue or violet color is a positive indication of the presence of free amines, including that the coupling reaction is not yet complete. If a positive ninhydrin test was observed after one hour of coupling reaction, the coupling reaction was continued for an additional hour. If a positive ninhydrin test occurred after 3 hours of coupling reaction, the vessel was drained, and the coupling was repeated using about one equivalent of activated amino acid and reagents.

Example 1

Preparation of Fmoc-Glu(OtBu)-Loaded 2-CTC Resin

To the nitrogen purged IL peptide reactor, charge 40 g 2-CTC resin and 400 mL DCM. Stir at 25±2° C. for 30 minutes. Meanwhile, charge to a 1 L flask, 9.7 g Fmoc-Glu (OtBu)OH, 280 mL DMF, 40 mL DCM and 5.5 g DIEA. Stir the contents at ambient temperature to dissolve the solids.

Drain the DCM from the reactor and charge the above prepared solution of Fmoc-Glu(OtBu)OH. Stir the mixture for 2 hours at 25±2° C. and drain the reactor.

Charge to the reactor, a mixture of DIEA:MeOH (40:360 mL). Stir the contents at 25±2° C. for one hour and drain the reactor.

Wash the resin bed with 1×400 mL DMF, 1×200 mL DMF, and 4×400 mL DCM.

Check the last wash for negative UV test.

Wash the resin bed with 3×400 mL Isopropanol. Vacuum dry the resin to a constant weight at 40±2° C.

Yield: 48.9 g
Loading Factor Analysis: 0.44 mmole/g
Ref. No. 408-146

Example 2

Solid Phase Synthesis of T-1249 intermediate fragment Ac-AA(1-20)OH (SEQ ID NO:2)

To a SPPS chamber, charge 25.0 g of Fmoc-Glu(OtBu)-O-2-CTC (Example 1) resin and 250 mL DCM. Stir the mixture for 30 minutes at 30±3° C. Drain the reactor and wash resin bed with 3×150 mL NMP. Charge to the reactor 125 mL 20% piperidine in NMP and stir at 30±3° C. for 30 minutes. Drain the reactor and charge 125 mL 20% piperidine in NMP. Stir the mixture for 30 minutes at 30±3° C. and drain the reactor.

Charge to a flask, 10.1 g Fmoc-Gln(Trt)OH, 2.82 g 6-Chloro HOBT, 2.45 g DIEA and 113 mL NMP. Stir the contents at ambient temperature to dissolve the solids and then cool to 10° C.

In a separate flask, charge 5.3 g TBTU and 68 mL NMP. Stir at ambient temperature to dissolve solids and cool to 110° C. Add cooled TBTU solution to the Fmoc-Gln(Trt)OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 3±3° C. for 30 minutes and drain the reactor. Wash the resin bed with 5×150 mL NMP. Sample the last wash for piperidine level by qualitative Ninhydrin test. Charge to a flask, 10.1 g Fmoc-Gln(Trt)OH, 2.84 g 6-Chloro HOBT, 2.45 g DIEA and 80 mL NMP. Stir the contents at ambient temperature to dissolve the solids and then cool to 10° C.

In a separate flask, charge 5.3 g TBTU and 68 mL NMP. Stir at ambient temperature to dissolve solids and cool to 10° C. Add cooled TBTU solution to the Fmoc-Gln(Trt)OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP. Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 5.83 g Fmoc-Ile-OH, 2.84 g 6-Chloro HOBT, 2.42 g DIEA and 113 mL NMP. Stir the contents at ambient temperature to dissolve the solids and then cool to 10° C.

In a separate flask, charge 5.3 g TBTU and 68 mL NMP. Stir at ambient temperature to dissolve solids and cool to 10° C. Add cooled TBTU solution to the Fmoc-Ile-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 11.75 g Fmoc-Gln(Trt)OH, 3.3 g 6-Chloro HOBT, 2.84 g DIEA and 113 mL NMP. Stir the contents at ambient temperature to dissolve the solids and then cool to 10° C.

In a separate flask, charge 5.3 g TBTU and 68 mL NMP. Stir at ambient temperature to dissolve solids and cool to 10° C. Add cooled TBTU solution to the Fmoc-Gln(Trt)OH solution and charge this solution to the SPPS reactor. Wash the flask with 50 mL DCM and charge the wash to the SPPS reactor. Stir the mixture at 303° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 5.45 g Fmoc-Ala-OH, 3.3 g 6-Chloro HOBT, 2.85 g DIEA and 113 mL NMP. Stir the contents at ambient temperature to dissolve the solids and then cool to 10° C.

In a separate flask, charge 6.18 g TBTU and 68 mL NMP. Stir at ambient temperature to dissolve solids and cool to 10° C. Add cooled TBTU solution to the Fmoc-Ala-OH solution and charge this solution to the SPPS reactor. Wash the flask with 50 mL DCM and charge the wash to the SPPS reactor. Stir the mixture at 303° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 11.75 g Fmoc-Gln(Trt)OH, 3.2 g 6-Chloro HOBT, 3.1 g DIEA and 113 mL NMP. Stir the contents at ambient temperature to dissolve the solids and then cool to 10° C.

In a separate flask, charge 7.9 g TBTU and 68 mL NMP. Stir at ambient temperature to dissolve solids and cool to 10° C. Add cooled TBTU solution to the Fmoc-Gln(Trt)OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 8.2 g Fmoc-Glu(OtBu)OH, 3.2 g 6-Chloro HOBT, 2.84 g DIEA and 113 mL NMP. Stir the contents at ambient temperature to dissolve the solids and then cool to 10° C.

In a separate flask, charge 6.18 g TBTU and 68 mL NMP. Stir at ambient temperature to dissolve solids and cool to 10° C. Add cooled TBTU solution to the Fmoc-Glu(OtBu)OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 303° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 5.83 g Fmoc-Leu-OH, 2.8 g 6-Chloro HOBT, 2.42 g DIEA and 113 mL NMP. Stir the contents at ambient temperature to dissolve the solids and then cool to 10° C.

In a separate flask, charge 5.3 g TBTU and 68 mL NMP. Stir at ambient temperature to dissolve solids and cool to 10° C. Add cooled TBTU solution to the Fmoc-Leu-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 5.83 g Fmoc-Leu-OH, 2.8 g 6-Chloro HOBT, 2.42 g DIEA and 113 mL NMP. Stir the contents at ambient temperature to dissolve the solids and then cool to 10° C.

In a separate flask, charge 5.3 g TBTU and 68 mL NMP. Stir at ambient temperature to dissolve solids and cool to 10° C. Add cooled TBTU solution to the Fmoc-Leu-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 5.14 g Fmoc-Ala-OH, 2.8 g 6-Chloro HOBT, 2.42 g DIEA and 113 mL NMP. Stir the contents at ambient temperature to dissolve the solids and then cool to 10° C.

In a separate flask, charge 5.3 g TBTU and 68 mL NMP. Stir at ambient temperature to dissolve solids and cool to 10° C. Add cooled TBTU solution to the Fmoc-Ala-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C.

for 30 minutes and drain the reactor. Wash the resin bed with 5×150 mL NMP. Sample the last wash for piperidine level by qualitative Ninhydrin test.

Charge to a flask, 6.6 g Fmoc-Thr(tBu)-OH, 2.8 g 6-Chloro HOBT, 2.42 g DIEA and 113 mL NMP. Stir the contents at ambient temperature to dissolve the solids and then cool to 10° C.

In a separate flask, charge 5.3 g TBTU and 68 mL NMP. Stir at ambient temperature to dissolve solids and cool to 10° C. Add cooled TBTU solution to the Fmoc-The(tBu)-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 5.83 g Fmoc-Ile-OH, 2.8 g 6-Chloro HOBT, 2.42 g DIEA and 113 mL NMP. Stir the contents at ambient temperature to dissolve the solids and then cool to 10° C.

In a separate flask, charge 5.3 g TBTU and 68 mL NMP. Stir at ambient temperature to dissolve solids and cool to 10° C. Add cooled TBTU solution to the Fmoc-Ile-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 7.73 g Fmoc-Lys(Boc)-OH, 2.8 g 6-Chloro HOBT, 2.42 g DIEA and 113 mL NMP. Stir the contents at ambient temperature to dissolve the solids and then cool to 10° C.

In a separate flask, charge 5.3 g TBTU and 68 mL NMP. Stir at ambient temperature to dissolve solids and cool to 110° C. Add cooled TBTU solution to the Fmoc-Lys(Boc)-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 303° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 13.44 g Fmoc-Gln(Trt)-OH, 3.73 g 6-Chloro HOBT, 3.13 g DIEA and 113 mL NMP. Stir the contents at ambient temperature to dissolve the solids and then cool to 10° C.

In a separate flask, charge 7.06 g TBTU and 68 mL NMP. Stir at ambient temperature to dissolve solids and cool to 10° C. Add cooled TBTU solution to the Fmoc-Gln(Trt)-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 9.36 g Fmoc-Glu(OtBu)-OH, 3.73 g 6-Chloro HOBT, 3.13 g DIEA and 113 mL NMP. Stir the contents at ambient temperature to dissolve the solids and then cool to 10° C.

In a separate flask, charge 7.06 g TBTU and 68 mL NMP. Stir at ambient temperature to dissolve solids and cool to 110° C. Add cooled TBTU solution to the Fmoc-Glu(OtBu)-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 µl NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 11.6 g Fmoc-Trp(Boc)-OH, 3.73 g 6-Chloro HOBT, 3.13 g DIEA and 113 mL NMP. Stir the contents at ambient temperature to dissolve the solids and then cool to 10° C.

In a separate flask, charge 7.06 g TBTU and 68 mL NMP. Stir at ambient temperature to dissolve solids and cool to 10° C. Add cooled TBTU solution to the Fmoc-Trp(Boc)-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 9.36 g Fmoc-Glu(OtBu)-OH, 3.73 g 6-Chloro HOBT, 3.13 g DIEA and 113 mL NMP. Stir the contents at ambient temperature to dissolve the solids and then cool to 10° C.

In a separate flask, charge 7.06 g TBTU and 68 mL NMP. Stir at ambient temperature to dissolve solids and cool to 10° C. Add cooled TBTU solution to the Fmoc-Glu(OtBu)-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C.

for 30 minutes and drain the reactor. Wash the resin bed with 5×150 mL NMP. Sample the last wash for piperidine level by qualitative Ninhydrin test.

Charge to a flask, 13.44 g Fmoc-Gln(Trt)-OH, 3.73 g 6-Chloro HOBT, 3.13 g DIEA and 113 mL NMP. Stir the contents at ambient temperature to dissolve the solids and then cool to 10° C.

In a separate flask, charge 7.06 g TBTU and 68 mL NMP. Stir at ambient temperature to dissolve solids and cool to 10° C. Add cooled TBTU solution to the Fmoc-Gln(Trt)-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 11.6 g Fmoc-Trp(Boc)-OH, 3.73 g 6-Chloro HOBT, 3.13 g DIEA and 113 mL NMP. Stir the contents at ambient temperature to dissolve the solids and then cool to 10° C.

In a separate flask, charge 7.06 g TBTU and 68 mL NMP. Stir at ambient temperature to dissolve solids and cool to 10° C. Add cooled TBTU solution to the Fmoc-Trp(Boc)-OH solution and charge this solution to the SPPS reactor. Wash the flask with 50 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×150 mL NMP.

Charge to the reactor 125 mL 20% piperidine in NMP and stir at 30±3° C. for 30 minutes. Drain the reactor and charge 125 mL 20% piperidine in NMP. Stir the mixture at 30±3° C. for 30 minutes and drain the reactor. Wash the resin bed with 5×150 mL NMP. Sample the last wash for piperidine level by qualitative Ninhydrin test.

Charge to a flask, 5.62 g acetic anhydride, 7.11 g DIEA and 100 mL NMP. Mix the solution and cool to 10° C. Add cooled acetic anhydride solution to the SPPS reactor, rinse the flask with 50 mL NMP and add wash to the reactor. Stir the mixture at 30±3° C. for 1 hour. Sample the resin beads for the completion reaction (Keiser Test). Once the reaction is completed, drain the reactor and wash the resin bed with 5×180 mL NMP. Wash the resin bed with 5×180 mL DCM, 5×180 mL Isopropanol. Vacuum dry the resin at 40±2° C.

Yield: 57.83 g
Ref. No. 408-149

Example 3

Cleavage and purification of Ac-AA(1-20)OH (SEQ ID NO:2) from solid phase resin

Charge to the SPPS reactor 30 g of above built resin and 300 mL DCM. Stir at ambient temperature for about 5 minutes. Drain the reactor and repeat the DCM wash one more time. Cool the reactor to −10±5° C.

Prepare a solution of 6 mL trifluoroacetic acid and 294 mL DCM. Cool the solution to 0±5° C.

Charge the cooled TFA solution to the reactor and stir the slurry for 45 minutes at 0±5° C. Add 7.6 mL pyridine and stir for additional 5 minutes at 0±5° C. Drain the reactor and wash the resin bed with 1×300 mL DCM, and 6×200 mL DCM at ambient temperature. Wash the DCM solution with 200 mL water. Concentrate DCM solution to about 40 mL volume and add 300 mL Isopropanol. Distill off DCM under 50 mm vacuum for 4 hours. Filter the product, wash with 2×100 mL Isopropanol (23 mL) and vacuum dry at 40±2° C.

Yield: 14.1 g (54.1%). A second crop of 7.85 g (30.1%) was obtained from mother liquors.

Example 4

Preparation of FmocTrp(Boc)-loaded 2-CTC Resin

A process was performed to prepare a FmocTrp(Boc)-loaded 2-CTC Resin.

To the nitrogen purged 1 L peptide reactor, charge 40 g 2-CTC resin and 400 mL DCM. Stir at 25±2° C. for 30 minutes. Meanwhile, charge to a 1 L flask, 12.66 g Fmoc-Trp (Boc)OH, 280 mL DMF, 40 mL DCM and 5.7 g DIEA. Stir the contents at ambient temperature to dissolve the solids.

Drain the DCM from the reactor and charge the above prepared solution of Fmoc-Trp(Boc)OH. Stir the mixture for 2 hours at 25±2° C. and drain the reactor.

Charge to the reactor, a mixture of DIEA:MeOH (40:360 mL). Stir the contents at 25±2° C. for one hour and drain the reactor. Wash the resin bed with 400 mL DMF, 200 mL DMF and 3×400 mL DCM. Check the last wash for negative UV test.

Wash the resin bed with 3×400 mL NMP and charge to the reactor 275 mL 20% piperidine in NMP. Stir the mixture at 28±2° C. for 30 minutes. Drain the reactor and repeat the step for another 30 minutes. Drain the reactor and wash resin bed with 5×300 mL NMP, 5×300 mL DCM and 3×300 mL Isopropanol. Vacuum dry the resin to a constant weight at 40±2° C.

Yield: 47.4 g
Loading Factor Analysis: 0.4 mmole/g
Ref No. 393-134

Example 5

Solid Phase Synthesis of T-1249 Intermediate Fragment Fmoc-AA(21-38)OH (SEQ ID NO:3)

To a SPPS chamber, charge 20.0 g of H-Trp(Boc)-O-2-CTC resin (Example 4) and 200 mL DCM. Stir the mixture for 30 minutes at 30±3° C. Drain the reactor and wash resin bed with 3×120 mL NMP.

Charge to a flask, 5.14 g Fmoc-Glu(OtBu)OH, 2.1 g 6-Chloro HOBT, 1.81 g DIEA and 54 mL NMP. Stir the contents at ambient temperature to dissolve the solids and then cool to 10° C.

In a separate flask, charge 3.88 g TBTU and 32 mL NMP. Stir at ambient temperature to dissolve solids and cool to 10° C. Add cooled TBTU solution to the Fmoc-Glu(OtBu)OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 6.33 g Fmoc-Trp(Boc)OH, 2.04 g 6-Chloro HOBT, 1.77 g DIEA and 54 mL NMP. Stir the contents at ambient temperature to dissolve the solids and then cool to 10° C.

In a separate flask, charge 3.86 g TBTU and 32 mL NMP. Stir at ambient temperature to dissolve solids and cool to 10° C. Add cooled TBTU solution to the Fmoc-Trp(Boc)OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 30±3° C. for 30 minutes. Drain the reactor and charge 100 mL 20% piperidine in NMP. Stir the mixture at 303° C. for 30 minutes and drain the reactor. Wash the resin bed with 5×120 mL NMP. Sample the last wash for piperidine level by qualitative Ninhydrin test.

Charge to a flask, 4.26 g Fmoc-Leu-OH, 2.04 g 6-Chloro HOBT, 1.81 g DIEA and 54 mL NMP. Stir the contents at ambient temperature to dissolve the solids and then cool to 10° C.

In a separate flask, charge 3.87 g TBTU and 32 mL NMP. Stir at ambient temperature to dissolve solids and cool to 10° C. Add cooled TBTU solution to the Fmoc-Leu-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 3×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 4.62 g Fmoc-Ser(tBu)-OH, 2.06 g 6-Chloro HOBT, 1.8 g DIEA and 54 mL NMP. Stir the contents at ambient temperature to dissolve the solids and then cool to 10° C.

In a separate flask, charge 3.88 g TBTU and 32 mL NMP. Stir at ambient temperature to dissolve solids and cool to 10° C. Add cooled TBTU solution to the Fmoc-Ser(tBu)-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 3×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 3.75 g Fmoc-Ala-OH, 2.05 g 6-Chloro HOBT, 1.76 g DIEA and 54 mL NMP. Stir the contents at ambient temperature to dissolve the solids and then cool to 10° C.

In a separate flask, charge 3.89 g TBTU and 32 mL NMP. Stir at ambient temperature to dissolve solids and cool to 10° C. Add cooled TBTU solution to the Fmoc-Ala-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 3×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 6.32 g Fmoc-Trp(Boc)-OH, 2.06 g 6-Chloro HOBT, 1.82 g DIEA and 54 mL NMP. Stir the contents at ambient temperature to dissolve the solids and then cool to 10° C.

In a separate flask, charge 3.87 g TBTU and 32 mL NMP. Stir at ambient temperature to dissolve solids and cool to 10° C. Add cooled TBTU solution to the Fmoc-Trp(Boc)-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 303° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 5.64 g Fmoc-Lys(Boc)-OH, 2.06 g 6-Chloro HOBT, 1.79 g DIEA and 54 mL NMP. Stir the contents at ambient temperature to dissolve the solids and then cool to 10° C.

In a separate flask, charge 3.87 g TBTU and 32 mL NMP. Stir at ambient temperature to dissolve solids and cool to 10° C. Add cooled TBTU solution to the Fmoc-Lys(Boc)-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 4×120 mL NMP. Sample the last wash for piperidine level by qualitative Ninhydrin test.

Charge to a flask, 4.95 g Fmoc-Asp(OtBu)-OH, 2.09 g 6-Chloro HOBT, 1.76 g DIEA and 54 mL NMP. Stir the contents at ambient temperature to dissolve the solids and then cool to 10° C.

In a separate flask, charge 3.88 g TBTU and 32 mL NMP. Stir at ambient temperature to dissolve solids and cool to 10° C. Add cooled TBTU solution to the Fmoc-Asp(OtBu)-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 4.25 g Fmoc-Leu-OH, 2.09 g 6-Chloro HOBT, 1.78 g DIEA and 54 mL NMP. Stir the contents at ambient temperature to dissolve the solids and then cool to 10° C.

In a separate flask, charge 3.86 g TBTU and 32 mL NMP. Stir at ambient temperature to dissolve solids and cool to 10° C. Add cooled TBTU solution to the Fmoc-Leu-OH solution and charge this solution to the SPPS reactor. Wash the flask with 24 mL DCM and charge the wash to the SPPS reactor. Stir the mixture at 303° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 6.40 g Fmoc-Lys(Boc)-OH, 2.33 g 6-Chloro HOBT, 2.13 g DIEA and 54 mL NMP. Stir the contents at ambient temperature to dissolve the solids and then cool to 10° C.

In a separate flask, charge 4.41 g TBTU and 32 mL NMP. Stir at ambient temperature to dissolve solids and cool to 110° C. Add cooled TBTU solution to the Fmoc-Lys(Boc)-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 8.35 g Fmoc-Gln(Trt)-OH, 2.33 g 6-Chloro HOBT, 2.09 g DIEA and 54 mL NMP. Stir the contents at ambient temperature to dissolve the solids and then cool to 10° C.

In a separate flask, charge 4.38 g TBTU and 32 mL NMP. Stir at ambient temperature to dissolve solids and cool to 10° C. Add cooled TBTU solution to the Fmoc-Gln(Trt)-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 4.83 g Fmoc-Leu-OH, 2.33 g 6-Chloro HOBT, 2.06 g DIEA and 54 mL NMP. Stir the contents at ambient temperature to dissolve the solids and then cool to 10° C.

In a separate flask, charge 4.37 g TBTU and 32 mL NMP. Stir at ambient temperature to dissolve solids and cool to 10° C. Add cooled TBTU solution to the Fmoc-Leu-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 3×120 mL NMP.

Charge to the reactor 100 mL 20% piperidine in NMP and stir at 303° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 5.81 g Fmoc-Glu(OtBu)-OH, 2.35 g 6-Chloro HOBT, 2.08 g DIEA and 54 mL NMP. Stir the contents at ambient temperature to dissolve the solids and then cool to 10° C.

In a separate flask, charge 4.39 g TBTU and 32 mL NMP. Stir at ambient temperature to dissolve solids and cool to 10° C. Add cooled TBTU solution to the Fmoc-Glu(OtBu)-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 303° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 6.29 g Fmoc-Tyr(OtBu)-OH, 2.33 g 6-Chloro HOBT, 2.11 g DIEA and 54 mL NMP. Stir the contents at ambient temperature to dissolve the solids and then cool to 10° C.

In a separate flask, charge 4.39 g TBTU and 32 mL NMP. Stir at ambient temperature to dissolve solids and cool to 10° C. Add cooled TBTU solution to the Fmoc-Tyr(OtBu)-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 3×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 5.81 g Fmoc-Glu(OtBu)-OH, 2.34 g 6-Chloro HOBT, 2.06 g DIEA and 54 mL NMP. Stir the contents at ambient temperature to dissolve the solids and then cool to 10° C.

In a separate flask, charge 4.37 g TBTU and 32 mL NMP. Stir at ambient temperature to dissolve solids and cool to 10° C. Add cooled TBTU solution to the Fmoc-Glu(OtBu)-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 5×120 mL NMP. Sample the last wash for piperidine level by qualitative Ninhydrin test.

Charge to a flask, 8.13 g Fmoc-Asn(Trt)-OH, 2.32 g 6-Chloro HOBT, 2.17 g DIEA and 54 mL NMP. Stir the contents at ambient temperature to dissolve the solids and then cool to 10° C.

In a separate flask, charge 4.37 g TBTU and 32 mL NMP. Stir at ambient temperature to dissolve solids and cool to 10° C. Add cooled TBTU solution to the Fmoc-Asn(Trt)-OH solution and charge this solution to the SPPS reactor. Wash the flask with 24 mL DCM and charge the wash to the SPPS reactor. Stir the mixture at 30±3° C. for 3 hours. Sample the resin beads for the completion reaction (Keiser Test). Once the reaction is completed, drain the reactor and wash the resin bed with 4×120 mL NMP.

Charge to the reactor 100 mL 20% piperidine in NMP and stir at 30±3° C. for 30 minutes. Drain the reactor and charge 100 mL 20% piperidine in NMP. Stir the mixture at 30±3° C. for 30 minutes and drain the reactor. Wash the resin bed with 4×120 mL NMP. Sample the last wash for piperidine level by qualitative Ninhydrin test.

Charge to a flask, 6.38 g Fmoc-Lys(Boc)-OH, 2.33 g 6-Chloro HOBT, 2.16 g DIEA and 54 mL NMP. Stir the contents at ambient temperature to dissolve the solids and then cool to 10° C.

In a separate flask, charge 4.39 g TBTU and 32 mL NMP. Stir at ambient temperature to dissolve solids and cool to 10° C. Add cooled TBTU solution to the Fmoc-Lys(Boc)-OH solution and charge this solution to the SPPS reactor. Wash the flask with 24 mL DCM and charge the wash to the SPPS reactor. Stir the mixture at 303° C. for 3 hours. Sample the resin beads for the completion reaction (Keiser Test). Kaiser test showed incomplete reaction. The resin bed was treated with 2.83 g Fmoc-Lys(Boc)OH, 1.04 g 6-Chloro HOBT, 1.01 g DIEA in 30 mL NMP. A solution of 1.94 g TBTU in 22 mL NMP was added and the mixture stirred for additional 3 hours and sampled. Once the reaction is completed, drain the reactor and wash the resin bed with 5×120 mL NMP. Wash the resin bed with 6×120 mL DCM, 4×120 mL Isopropanol. Vacuum dry the resin at 40±2° C.

Yield: 46.77 g

Example 6

Cleavage and Purification of Fmoc-AA(21-38)OH (SEQ ID NO:3)from Solid Phase Resin Cleavage of Fmoc-Lys-Asn-Glu-Tyr-Glu-Leu-Gln-Lys-Leu-Asp-Lys-Trp-Ala-Ser-Leu-Trp-Glu-Trp-O-2-CTC Resin [Fragment Fmoc-AA(21-38)0-2-CTC Resin]

Charge to the SPPS reactor 200 mL 2% v/v Trifluoroacetic acid/DCM solution. Cool the solution to 0±5° C. and add 20.02 g of Fmoc-AA(21-38)—O-2-CTC Resin. Stir the mixture for 45 minutes. Add 5.1 mL Pyridine and warm the mixture to ambient temperature. Drain the reactor and wash the resin bed with 7×100 mL DCM. Wash the combined DCM washes with 2×250 mL water. Concentrate the DCM solution under vacuum to about 250 mL volumes. Add 250 mL Heptane and continue distillation until additional 200 mL distillate is collected. Add 250 mL Heptane and continue distillation until product precipitates. Filter the product and wash with 3×50 Heptane. Suspend the wet cake in 250 mL Heptane, and stir at ambient temperature for 30 minutes. Filter the product and wash with 2×75 mL Heptane. Vacuum dry the product.

Yield: 12.34 g (89.8%)

Example 7

Solution Phase Synthesis of H-AA(21-39)NH$_2$ (SEQ ID NO:4)

T-1249 intermediate fragment H-AA(21-39)NH$_2$ was prepared by solution phase coupling of PheNH$_2$ to Fmoc-AA (21-38)OH Preparation of H-AA(21-39)NH$_2$ was carried out starting with 3.00 g of Fmoc-AA(21-38)OH. Fmoc-AA(21-38)OH, as described in Example 6, (3.00 g), PheNH$_2$—HCl (0.74 g, 3.68 mmol, 1.3 eq.), and 6-chloro HOBT (0.96 g, 5.66 mmol, 2.0 eq.) were dissolved in DMF (100 mL, 8.3 vol.). The solution was cooled to −10° C. and DIEA (1.4 mL, 7.92 mmol, 2.8 eq.) in DMF (5 mL, 3.6 vol.) was added. TBTU (1.2 g, 3.68 mmol, 1.3 eq.) was added in one portion followed by DMF (15 mL,) rinse. The reaction mixture was stirred −10° C. overnight and warmed to ambient temperature. Stirring continued for additional 4 hours. The completion of the reaction was monitored by HPLC analysis which showed 0.4% starting Fmoc-AA(21-38)OH remaining. Piperidine (1.23 mL, 14.43 mmol, 5.1 eq.) was added and the solution was stirred at 30° C. for 3 hours. The completion of Fmoc removal was monitored by HPLC analysis which showed <1% Fmoc-AA(21-38)NH$_2$. Water (100 mL, 8.3 vol.) was added to precipitate the product. The solid was collected by suction filtration, washed with water. Drying overnight at ambient temperature afforded 11.85 g (101%, % AN HPLC).

Intermediate Fmoc-AA(21-39)NH$_2$ was treated with piperidine to remove Fmoc protecting group and the product H-AA(21-39)NH$_2$ was isolated by suction filtration. The wet cake was suspended in 1:1 EtOH:Water for 30 minutes. Filtration followed by another re-slurry in 1:2 MTBE:Heptane and drying gave 2.67 g (90.7%) of H-AA(21-39)NH$_2$ with a purity of 84.1% (AN HPLC).

HPLC Conditions:

Column: Betabasic C-18, 150×4.6 mm, 3 μm, 150 Å

Flow rate: 1.5 mL/min

Detection: UV at 262 nM

Mobile phase: A: 0.15% TFA/water

B: 0.05% TFA/ACN

C: 0.05% TFA/THF

Retention time: Approximately 12 minutes

Example 8

Solution Phase Synthesis of Ac-AA(1-39)NH$_2$ (SEQ ID NO:1)

T-1249 final product was prepared by solution phase coupling of Ac-AA(1-20)OH with H-AA(21-39)NH$_2$.

H-AA(21-39)NH$_2$ (2.07 g, 0.53 mmol, 1.2 eq.), Ac-AA(1-20)OH (2.0 g, 0.44 mmol, 1 eq.), and 6-chloro HOBT (0.15 g, 0.89 mmol, 2.0 eq.) were dissolved in DMF (33 mL, 16 vol., 15 minutes). The solution was cooled to 0±5° C. and DIEA (0.16 g, 1.3 mmol, 3.0 eq.) followed by TBTU (0.0.18 g, 0.57 mmol, 1.3 eq.) were added. After stirring at 0° C. for 1.5 hours, the solution was warmed to ambient temperature and stirred until the reaction was complete. Water (40 mL) was added dropwise. The resulting slurry was stirred at ambient temperature for 0.8 hours and the product was isolated by suction filtration. Drying overnight at ambient temperature gave 4.07 g (95.1%) of Ac-AA(1-39)NH$_2$ with a purity of 72.1% (AN HPLC).

HPLC Conditions:
Column: Betabasic C-18, 150×4.6 mm, 3 µm, 150 Å
Flow rate: 1.5 mL/min
Detection: UV at 262 nM
Mobile phase: A: 0.15% TFA/water
  B: 0.05% TFA/ACN
  C: 0.05% TFA/THF
Retention time: Approximately 25 minutes

Example 9

Preparation of T-1249 by side-chain deprotection of Ac-AA(1-39)NH$_2$

Ac-AA(1-39)NH$_2$ (5.00 g) was dissolved in DCM (50 mL, 10 vol.) and treated with 35 mL of a freshly prepared solution of TFA:DTT:water (35 mL TFA:2.52 g DTT:0.85 mL water). The solution was stirred at ambient temperature for 6.5 hours and cooled to 0±5° C. MTBE (150 mL) was added and the precipitates collected by suction filtration. The fine powder was suspended in a solution of acetonitrile (130 mL), DIEA (2.6 mL), acetic acid (1.91 mL) and water (5.6 mL). The slurry was stirred at 40° C. overnight to allow for decarboxylation of the indole side-chain of the tryptophans, cooled to ambient temperature and product was collected by suction filtration. Drying overnight in a vacuum oven at ambient temperature gave 2.98 g (100.4%) of T-1249. The purity of T-1249 was 61% (AN) and 42% (wt./wt.).

HPLC Conditions:
Column: Betabasic C-18, 150×4.6 mm, 3 µm, 3 µm
Flow rate: 1.6 mL/min
Detection: UV at 220 nM
Mobile phase: A: 0.10% TFA in water/0.075% TFA in ACN/MeOH, 55/41/0.4
  B: 0.10% TFA in water/0.075% TFA in CAN/MeOH, 42/54/0.4
  C: 0.075% TFA in ACN
Retention time: Approximately 9 minutes

---

What is claimed is:

1. A method of preparing a peptide having the sequence WQEWEQKITALLEQAQIQQEKNEYELQKLDKWASLWEWF (SEQ ID NO:1) comprising the steps of:
   (a) providing peptide intermediate fragments WQEWEQKITALLEQAQIQQE (SEQ ID NO:2) and KNEYELQKLDKWASLWEW (SEQ ID NO:3), wherein SEQ ID NO:2 and SEQ ID NO:3 have been synthesized on solid supports utilizing a loading factor of 0.5 or less;
   (b) in solution phase, reacting KNEYELQKLDKWASLWEW (SEQ ID NO:3) with phenylalaninamide to provide KNEYELQKLDKWASLWEWF (SEQ ID NO:4); and
   (c) in solution phase, reacting WQEWEQKITALLEQAQIQQE (SEQ ID NO:2) with KNEYELQKLDKWASLWEWF (SEQ ID NO:4) to provide WQEWEQKITALLEQAQIQQEKNEYELQKLDKWASLWEWF (SEQ ID NO:1).

2. The method of claim 1 wherein step (a), the peptide intermediate fragments have been synthesized on solid supports utilizing a loading factor of less than 0.5.

3. The method of claim 2 wherein step (a), the peptide intermediate fragments have been synthesized on solid supports utilizing a loading factor between 0.2 and 0.5.

4. The method of claim 2 wherein step (a), the peptide intermediate fragments have been synthesized on solid supports utilizing a loading factor in the range of 0.2-0.45.

5. The method of claim 4 wherein step (a), the peptide intermediate fragments have been synthesized on solid supports utilizing a loading factor in the range of 0.25-0.40.

6. The method of claim 1 wherein step (a), the peptide intermediate fragments have been synthesized on solid supports utilizing amino acids having been coupled to the support in an amount between 1 and 1.5 equivalents.

* * * * *